(12) United States Patent
Bagabas et al.

(10) Patent No.: US 7,951,976 B1
(45) Date of Patent: May 31, 2011

(54) SYNTHESIZING AND UTILIZING NOVEL NANO CRYSTALLINE ZINC CHROMATE SUPPORTED NANO PALLADIUM CATALYST

(75) Inventors: Abdulaziz Ahmed Bagabas, Riyadh (SA); Vagif Melik Akhmedov, Baku (AZ); Abdulrahman Al-Rabiah, Riyadh (SA); Mohamed Mokhtar Mohamed Mostafa, Cairo (EG)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 0 days.

(21) Appl. No.: 12/856,653

(22) Filed: Aug. 15, 2010

(51) Int. Cl.
*C07C 45/72* (2006.01)
*C07C 27/00* (2006.01)
*B01J 23/06* (2006.01)
*B01J 23/60* (2006.01)

(52) U.S. Cl. ........ 568/388; 568/878; 502/307; 502/329; 502/343

(58) Field of Classification Search ........... 568/388; 502/307, 329, 343
See application file for complete search history.

(56) References Cited

U.S. PATENT DOCUMENTS

| | | | | |
|---|---|---|---|---|
| 5,811,365 | A * | 9/1998 | Barry | 502/343 |
| 7,482,382 | B2 * | 1/2009 | Li et al. | 516/33 |
| 2010/0135937 | A1 * | 6/2010 | O'Brien et al. | 424/59 |
| 2011/0002970 | A1 * | 1/2011 | Parashar | 424/401 |

OTHER PUBLICATIONS

Fahd Al-Wadaani et al., Pd supported on ZnII-CrIII mixed oxide as a catalyst for one-step synthesis of methyl isobutyl ketone, Journal of Catalysis 2008, vol. 257, 199-205.

Elena F. Kozhevnikova et al., One-step synthesis of methyl isobutyl ketone from acetone catalysed by Pd supported on ZnII-CrIII mixed oxide, Journal of Catalysis 2006, vol. 238, 286-292.

* cited by examiner

*Primary Examiner* — Sikarl A Witherspoon
(74) *Attorney, Agent, or Firm* — Geeta Kadambi Riddhi IP LLC (57) ABSTRACT

Several metal-supported catalyst compositions based on nano-crystalline zinc oxide were synthesized and characterized by X-ray powder diffraction (XRD), Carbon dioxide temperature programmed desorption ($CO_2$ TPD), and nitrogen adsorption at −196° C. The Pd-supported nano-ZnO mixed with different oxides such as $Cr_2O_3$, $CrO_3$, MgO, and $\gamma$-$Al_2O_3$ showed high catalytic activity in acetone condensation in gas-phase process under hydrogen flow. This reaction involves the base-acid coupling of acetone to form mesityl oxide, followed by its hydrogenation to methyl isobutyl ketone (MIBK). The novel catalyst 1% wt. n-Pd/n-$ZnCr_2O_4$ was utilized during gas-phase reaction during production of MIBK. MIBK selectivity was 70-72% at 66-77% acetone conversion at 300-350° C. Diisobutyl ketone (DIBK) was the main by-product, with a total MIBK+DIBK selectivity up to 88%. The prepared catalysts showed stable activity and may be used repeatedly and for a longer period of time.

20 Claims, 6 Drawing Sheets

(PRIOR ART)

SYNTHESIZING AND UTILIZING NOVEL NANO CRYSTALLINE ZINC CHROMATE SUPPORTED NANO PALLADIUM CATALYST

FIELD OF TECHNOLOGY

This disclosure generally relates to synthesizing a novel nano-crystalline zinc chromite-supported nano-palladium catalyst and using the said novel catalyst to increase the production of methyl isobutyl ketone (MIBK).

BACKGROUND

Aldol condensation is a vital tool in organic synthesis to create carbon-carbon bond between two aldehyde or ketone molecules. The aldol product (β-hydroxyaldehyde or β-hydroxyketone) possesses hydroxyl and carbonyl functional groups, enabling its conversion via successive reactions to numerous industrially important products such as diols, α,β-unsaturated aldehydes, α,β-unsaturated ketones, saturated alcohols, allylic alcohols, aldehydes, and ketones. However, the aldol condensation is a reversible process, a feature that limits the utility of this reaction in term of conversion, especially when the starting material is a ketone because of unfavourable equilibrium. Acetone condensation is an example for the synthesis of highly important products such as methyl isobutyl ketone (MIBK), diisobutyl ketone (DIBK), phorone (PH), and α-isophorone (IPH) with low acetone conversion and low selectivity for the desired product.

Figure 1:
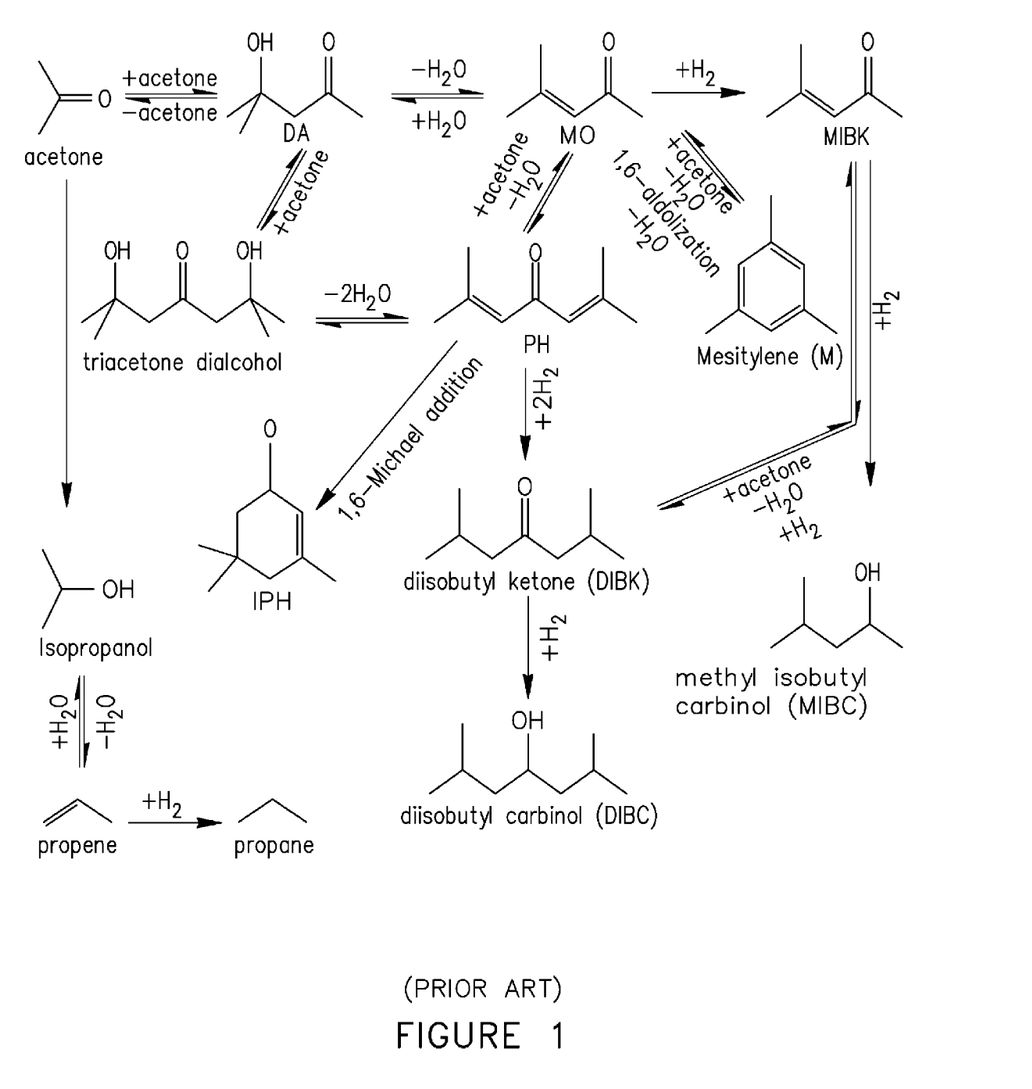
FIG. 1 main reaction pathways in acetone condensation process.

MIBK is an important product derived from acetone. It is used as a solvent in paint and protective coating systems. MIBK is commercially produced using a three-step process. The main reaction pathways for the synthesis of MIBK from acetone are shown in FIG. 1. The first step is the aldol addition of acetone to diacetone alcohol (DA, 4-hydroxy-4-methyl-2-pentanone). The second step is the aldol condensation of DA to mesityl oxide (MO, 4-methyl-3-penten-2-one). The final step is the selective hydrogenation of the carbon-carbon olefinic bond of MO to form MIBK. The most commonly observed side reactions are over-condensation and unselective hydrogenations.

Numerous catalysts are currently used in gas or liquid phase production of MIBK to obtain high yield with little success. The atmosphere, temperature and reaction phase play a vital role in the final yield of the MIBK.

The production processes are complicated and operational costs are high. The use of homogeneous liquid base and acid catalysts create a corrosive environment, require an additional neutralization process for their disposal, and generate a significant wastewater stream. Furthermore, the separation of DA and MO is mandatory for carrying out its successive step. Thus, there is a need for a better catalyst, which can be used in gas-phase production as well as in liquid phase production of MIBK. The MIBK production should provide a higher yield and, in turn, should become cost effective.

SUMMARY

The invention discloses a method of synthesizing a novel nano-crystalline zinc chromite-supported nano-palladium catalyst to increase the production of MIBK and other by products via one-step, gas-phase acetone self-condensation process.

In one embodiment, method of making a nano-crystalline zinc chromite-supported nano-palladium is described. Various combinations of platinum group metals and others were tested with zinc oxide. Several metals and different concentrations were tried to obtain a stable and effective catalyst.

In one embodiment, influence of the acid and basic properties of nano ZnO-based catalysts on the activity and selectivity for acetone condensation to MIBK was evaluated. In another embodiment, nano-ZnO was mixed with a metal oxide as an acid-base component and a platinum group metal as a hydrogenation component.

In another embodiment, characterizations of several properties of the novel nano-crystalline zinc chromite-supported nano-palladium catalyst were performed. This characterization was done to prove the purity and efficacy of the novel catalyst and to prove the current methods efficiency and effectiveness.

Other features of the present embodiments will be apparent from the accompanying figures, tables and from the detailed description that follows.

DETAILED DESCRIPTION

Several methods of synthesizing a novel nano-crystalline zinc chromite-supported nano-palladium catalyst and utilizing the novel catalyst to increase the production of MIBK and other by products are disclosed. Although the present embodiments have been described with reference to specific example embodiments, it will be evident that various modifications and changes may be made to these embodiments without departing from the broader spirit and scope of the various embodiments.

Preparation of Nano-Zinc Oxide:

Nano-zinc oxide (n-ZnO) was prepared with average crystallite size of 24.6 nm and BET specific surface area of 37.37 $m^2/g$ from zinc sulfate heptahydrate (BDH, 99.5%), sodium pyruvate (Sigma-Aldrich, ≧99%), sodium hydrogen carbonate (Fluka, ≧99.5%), hydroxylamine hydrochloride (Carlo Erba, 99%), and deionized water (18.2 MΩ·cm), obtained from a Milli-Q water purification system (Millipore). These chemicals were reacted with each other according to the weight ratio and number of moles shown in Table 1. Thermal decomposition of the zinc derivative of pyruvic acid oxime at 389° C. was performed to eventually get n-ZnO.

TABLE 1

Weight ratio and mole ratio for the chemicals used to prepare n-ZnO.

| Chemical Compound | Weight Ratio | Mole Ratio |
|---|---|---|
| Zinc sulfate heptahydrate | 2.07 | 1 |
| Sodium Pyruvate | 1.58 | 2 |
| Sodium hydrogen carbonate | 1.22 | 2 |
| Hydroxylamine hydrochloride | 1.00 | 2 |

In another embodiment, optimization of a gas phase process of highly selective conversion of acetone to MIBK using nano-crystalline zinc chromite-supported nano-palladium catalyst was performed.

The novel catalyst composition, method of synthesizing the novel catalyst and method of utilizing the novel catalyst in chemical reactions disclosed herein may be implemented in any means for achieving various aspects. Other features will be apparent from the accompanying figures and from the detailed description that follows.

BRIEF DESCRIPTION OF THE DRAWINGS

Example embodiments are illustrated by way of example and no limitation in the tables and in the accompanying figures, like references indicate similar elements and in which.

The selectivity towards MIBK depends on the relative rates of above shown steps of acetone condensation. According to the chemical nature of different steps, aldol addition of acetone to DA is catalyzed by either basic or acidic sites, the aldol condensation of DA to MO is acid- or base-catalyzed, and the selective hydrogenation of MO to MIBK requires metal sites.

In the present study, n-ZnO itself, and mixed with different metal oxides were chosen as acid-base components and platinum group metals for e.g. ruthenium, rhodium, palladium, osmium, iridium, and platinum etc., were used as hydrogenation component. The acetone self-condensation was studied in a fixed-bed flow reactor at 250-350° C., normal pressure, and H$_2$/acetone 2:1 mole ratio. The metal loading on catalysts was 1 wt %.

The textural properties named surface area ($S_{BET}$), pore diameter; basic site density, crystalline phases, and crystallite size of some catalysts used in this investigation are displayed in Table 2.

TABLE 2

N$_2$ adsorption, CO$_2$ TPD and XRD characterization data.

| Catalyst | $S_{BET}$, m$^2$/g | BJH average pore diameter, nm | CO$_2$ ads., mmol/g | $n_b$,* mmol/ m$^2 \times 10^{-2}$ | Crystalline Phase | Average crystallite size, nm |
|---|---|---|---|---|---|---|
| 1%Pd/nano ZnO | 33 | — | 0.281 | 0.85 | ZnO (zincite) | 29 |
| 1%Pd/nano ZnO/ MgO | 32 | 43.5 | 3.446 | 10.70 | ZnO (zincite) | 24 |
| 1%Pd/ZnO/Cr$_2$O$_3$/ Li$_2$O (1:10:1) | 120 | 4.7 | 1.006 | 0.84 | amorphous | — |
| 1%Pd/nanoZnO/γ-Al$_2$O$_3$ | 61 | 38.9 | 0.669 | 1.09 | ZnO (zincite) | 21 |

*Base site density by TPD of CO$_2$.

Figure 6:
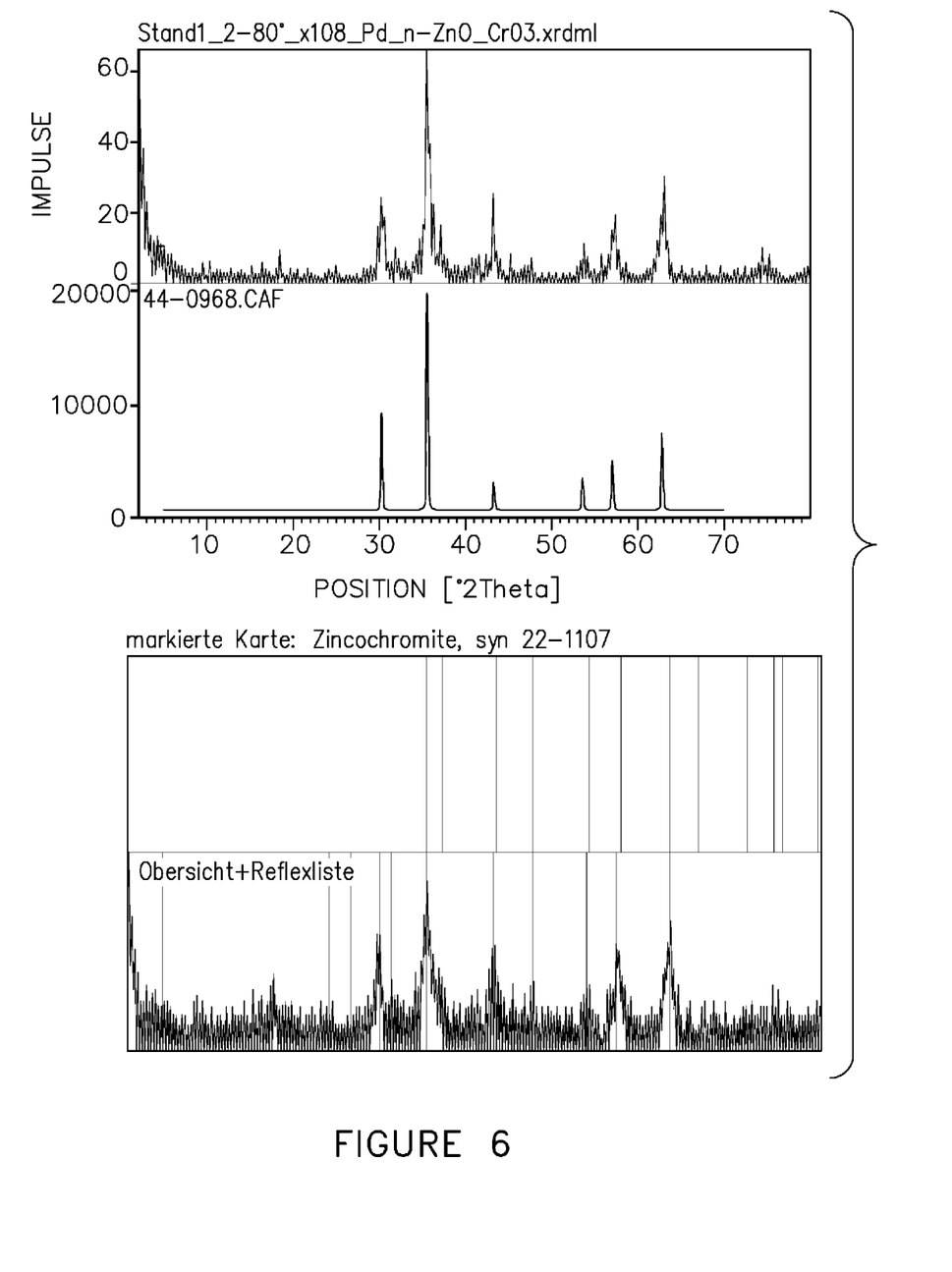

FIG. 6 shows XRD pattern of 1% wt. n-Pd/n-ZnCr$_2$O$_4$ catalyst and its match with database PDF No. 22-1107 of zinc chromite.

PREPARATION OF N-ZNO MIXTURE WITH OTHER METAL OXIDES

The n-ZnO itself and its mixtures with different metal oxides such as γ-alumina, chromium(III) oxide, chromium (VI) oxide, magnesium oxide, and zeolites (ZSM-5 and USY) were used as supports. Metal oxides first were calcinated at 350° C. for 5 hours under nitrogen flow. After calcination, they were mixed with nano zinc oxide in different ratios by mechanical stirring. These mixed metal oxides powder were then stirred with 0.02 M solution of metal salt at room temperature, followed by slow evaporation of the solvent in a rotary evaporator. The resulting powders were then reduced under hydrogen flow (50-60 ml/min) at 350° C. for 5 hours, which eventually led to the formation of the required catalysts.

Surface area and pore diameter, of these catalysts were measured by N$_2$ adsorption at −196° C. using Autosorb-1-MP (Quantachrome, U.S.A) instrument. The basicity was estimated from CO$_2$ TPD obtained on TPD/R/O 1100 Thermo Electron instrument. X-ray powder diffraction (XRD) was recorded, on a Philips X' pert pro diffractometer operated at 40 Kv by 40 mA using CuK$_\alpha$ radiation in the 2 theta range from 2 to 100° in steps of 0.02° with a sampling time of 1 s per step, for phase analysis and crystallite size measurement. The crystallite size was estimated using Scherer's equation. The reaction products (liquid and gas) were analyzed by gas chromatograph (GC) technique.

From the results displayed in Table 1, it can be noticed that the n-ZnO-based catalysts have average crystallite size similar to that for n-ZnO itself, indicating that loading of Pd on and mixing this catalyst with other oxide in 1 wt % do not affect the crystallite size. Zincite phase was only observed for these catalysts and no Pd metal patterns were observed, indicating the presence of a very fine dispersion of Pd on the surface of this support. Such an observation was reported previously for Pd over mixed Zn—Cr oxide supports (Kozhevnikova et al.). The surface areas of the first catalysts in Table 1 are similar to that of n-ZnO itself. However, mixing the n-ZnO with 1 wt % γ-Al$_2$O$_3$ resulted in a surface area as twice as that of the nano ZnO and as those of the first two catalysts in Table 1. This increase in surface area can be attributed to the addition of the fine powder of γ-Al$_2$O$_3$. The mixed Zn—Cr$^{3+}$—Li oxide has the highest surface area due to its amorphous nature. Such high surface area has been reported for mixed Zn—Cr$^{3+}$ oxide supports (Wadaani et al., Kozhevnikova et al.). The base site density ($n_b$) values for the first and third catalysts in Table 1 are similar and lower than the base densities of the other two catalysts containing γ-Al$_2$O$_3$ and MgO. The Pd/ZnO/MgO catalyst has the highest $n_b$ due to the presence of MgO, which is well-known for its basicity.

Preparation of Nano-Crystalline Zinc Chromite-Supported Nano-Palladium:

The synthesized n-ZnO was mixed and pulverized with the commercially available chromic oxide (CrO$_3$, Fluka) in a 1:1 mole ratio and with an appropriate amount of palladium acetate [Pd(OOCCH$_3$)$_2$, Aldrich], which yields 1% wt loading of palladium nanoparticles after the reduction process under hydrogen atmosphere (99.999%, Abdullah Hashim, Ltd.). Table 3 shows an example of the weight ratio and mole ratio used for Mixing the n-ZnO, CrO$_3$, and Pd(OOCCH$_3$)$_2$. Anhydrous, thiophene-free benzene (25 ml, Fisher Scientific) was added to this solid mixture to dissolve Pd(OOCCH$_3$)$_2$. The resultant suspension was mechanically stirred. Benzene was evaporated under vacuum at ambient temperature, over a period of 24 hours, by using a rotary evaporator. After drying, benzene was added and subsequently was evaporated twice more to ensure the homogeneous distribution of the palladium nanoparticle on the support of the final catalyst. After the third drying process, the resultant solid was ground and then was heated under a hydrogen flow of 50 ml/min at 350° C. for five hours in a digital, programmable, tubular muffle furnace. The temperature was ramped from the ambient to the target at a rate of 10° C./min. Cooling to the ambient was also performed at the same rate of heating. The obtained catalyst [1% wt. n-Pd/n-ZnCr$_2$O$_4$] after this reduction process was kept under hydrogen in desiccators until its use. The weight in gram could be n-ZnO between the range of 0.5 g to 2.0 g, CrO$_3$ between the range of 0.5 to 2.0 g and Pd(OOCCH$_3$) between the range of 0.01-1.0 g. These are suggested range and limitations.

TABLE 3

Weight quantities and number moles of n-ZnO, CrO3, and Pd(OOCCH$_3$)$_2$.

| Chemical Compound | Weight Ratio | Mole Ratio |
|---|---|---|
| n-ZnO | 21.10 | 54.33 |
| CrO$_3$ | 25.92 | 54.33 |
| Pd(OOCCH$_3$)$_2$ | 1.00 | 1.00 |

Characterization of this catalyst by X-ray powder diffraction (XRD) technique showed a pattern of broad peaks, matched with that of zinc chromite [ZnCr$_2$O$_4$] (FIG. 6). The broadness of the peaks implies the formation of nanocrystalline phase, which was confirmed by the average crystallite size of 18.65 nm, estimated by applying the Scherrer's equation to four peaks, as it displayed in Table 4.

TABLE 4

Calculation of the average crystallite size of the ZnCr$_2$O$_4$ phase of the 1% wt. n-Pd/n-ZnCr$_2$O$_4$ catalyst, based on Scherrer's equation.

| 2-Theta | Crystallite Size (nm) |
|---|---|
| 30.2 | 16.46 |
| 35.7 | 16.70 |
| 43.2 | 21.37 |
| 75.25 | 20.07 |

Average crystallite size = (16.46 + 16.70 + 21.37 + 20.07)/4 = 18.65 nm

Furthermore, observation of the chromite phase had the implication of reducing the hexavalent chromium [Cr(VI)] to the trivalent chromium [Cr(III)] under the reduction conditions, applied for the catalyst preparation, as illustrated in the following chemical equation:

$$\text{n-ZnO}_{(c)} + 2\text{Cr}^{VI}\text{O}_{3(c)} + 3\text{H}_{2(g)} \xrightarrow{350° \text{C.}} \text{n-ZnCr}_2^{III}\text{O}_{4(c)} + 3\text{H}_2\text{O}_{(g)} \quad \text{Eq. (1)}$$

This XRD spectrum (FIG. 6), in addition, did not display any characteristic patterns due to palladium metal. Such observation implies the formation of highly dispersed palladium metal nanoparticles. The reduction of the palladium bivalent to the zero-valent metallic palladium nanoparticles by hydrogen is illustrated in equation 2 below:

$$\text{Pd(OOCCH}_3)_{2(c)} + \text{H}_{2(g)} \xrightarrow{350° \text{C.}} \text{n-Pd}_{(c)} + 2\text{HOOCCH}_{3(g)} \quad \text{Eq. (2)}$$

The formation of nanocrystalline zinc chromite-supported nano-palladium catalyst can be given by the summation of equation 1 and equation 2, as represented in equation 3:

$$\text{Pd(OOCCH}_3)_{2(c)} + \text{n-ZnO}_{(c)} + 2\text{Cr}^{VI}\text{O}_{3(c)} + 4\text{H}_{2(g)} \xrightarrow{350° \text{C.}} \text{n-Pd/n-ZnCr}_2^{III}\text{O}_{4(c)} + 2\text{HOOCCH}_{3(g)} + 3\text{H}_2\text{O}_{(g)} \quad \text{Eq. (3)}$$

Catalytic Gas-Phase Acetone Self-Condensation:

The acetone self-condensation was performed in a temperature range of 250-350° C., under atmospheric pressure, in a tubular glass fixed-bed microreactor (ID 0.9 cm), under H$_2$ or N$_2$ atmosphere at a H$_2$/acetone mole ratio of 2. The reactor was placed in a vertical tubular furnace. A catalyst sample (~0.25 g) was loaded into the reactor between two layers of Pyrex glass wool and pieces of ceramics. A K-type thermocouple was placed in the center of the catalyst to monitor the reaction temperature. Acetone was introduced to the reactor by a Hitachi HPLC pump (Model L-2100/2130), connected to a heated tube (65-70° C.) for its delivery as a vapor mixed with H$_2$ or N$_2$ before entering the reaction zone at the top of the catalyst bed. The acetone was pumped at a continuous flow. The reaction liquid products were trapped at −40° C., were collected every one hour, and were analyzed off-line by using a Varian. CP-3800 gas chromatograph, equipped with a flame ionization detector (FID) and a 50 m×0.32 mm×1.2 mm CP-Wax 58 CB column. The gaseous downstream flow was analyzed online by a refinery gas analyzer (RGA) Varian CP-3800 GC, equipped with an FID and a thermal conductivity detector (TCD). The products were identified by GC, using authentic samples.

MIBK was the major reaction product and a significant amount of diisobutyl ketone (DIBK) was also formed. Maximum selectivity for MIBK was observed at 300-350° C. (Table 5). By-products included isopropyl alcohol (IPA) and other acetone condensation compounds such as mesitylene (M), DA, IPH, and PH. In the gaseous phase, a small amount of propene and propane were also detected.

TABLE 5

Gas-phase condensation of acetone on nano ZnO-based catalysts.

| Catalyst | Temp., °C. | Conv., % | Selectivity, % | | | | | | |
|---|---|---|---|---|---|---|---|---|---|
| | | | MIBK | DIBK | MO | M | IPA | DA | Others |
| Nano ZnO | 300 | 20.9 | 2.0 | trace | 55.8 | 2.6 | 9.5 | 1.4 | 28.7 |
| Nano ZnO* | 300 | 7.1 | 5.8 | trace | 73.7 | 1.3 | trace | trace | 19.2 |
| 1%Pd/nano ZnO | 300 | 53.9 | 56.2 | 22.4 | 2.3 | 3.2 | 7.6 | 3.5 | 4.9 |
| 1%Pd/nano ZnO* | 300 | 10.3 | 3.5 | 1.4 | 87.1 | 1.2 | 3.5 | trace | 3.3 |
| 1%Pd/ZnO/Cr$_2$O$_3$ (1:10) | 300 | 60.2 | 42.4 | 28.7 | 1.9 | 5.6 | 2.5 | 11.1 | 7.8 |
| 1%Pd/ZnO/Cr$_2$O$_3$/MgO (1:10:1) | 300 | 74.7 | 41.8 | 26.9 | 1.1 | 5.7 | 2.2 | 10.4 | 11.9 |
| 1%Pd/nano ZnO/CrO$_3$ (1:1) | 300 | 66.1 | 69.4 | 12.4 | 2.1 | 4.6 | 3.9 | 3.9 | 4.0 |
| 1%Pd/nano ZnO/CrO$_3$ (1:1) | 350 | 77.3 | 72.1 | 13.5 | 2.2 | 2.7 | 4.4 | 2.5 | 2.6 |
| 1%NiRe/ZSM-5/Al$_2$O$_3$ | 300 | 23.8 | 44.2 | 12.3 | 8.6 | 0.7 | 3.9 | 4.6 | 25.7 |
| 1%Pt/USY | 300 | 9.7 | 60.9 | trace | 4.4 | 7.3 | trace | trace | 27.4 |

Reaction conditions: 0.25 g catalyst, 15 ml/min H$_2$ flow, hydrogen/acetone = 2/1 mol, time on stream-1 hr.
*N$_2$ was used instead of H$_2$ (15 ml/min).

Figure 2:
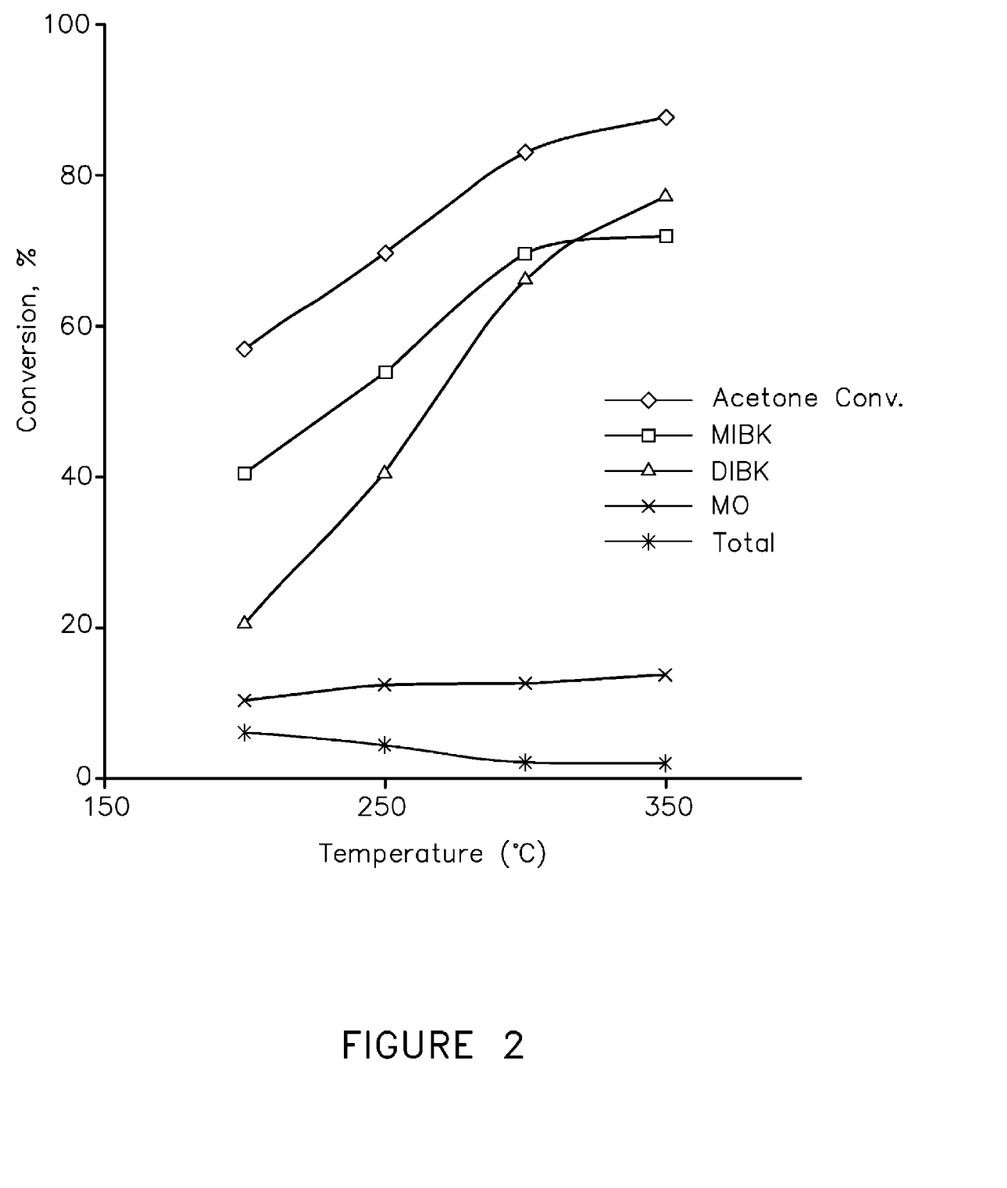
FIG. 2 shows acetone conversion and product selectivity's vs. reaction temperature on 1% wt. n-Pd/n-ZnCr$_2$O$_4$ (0.25 g catalyst, 15 ml/min H$_2$ flow, hydrogen/acetone=2/1 mol, time-1 hr).
Figure 3:
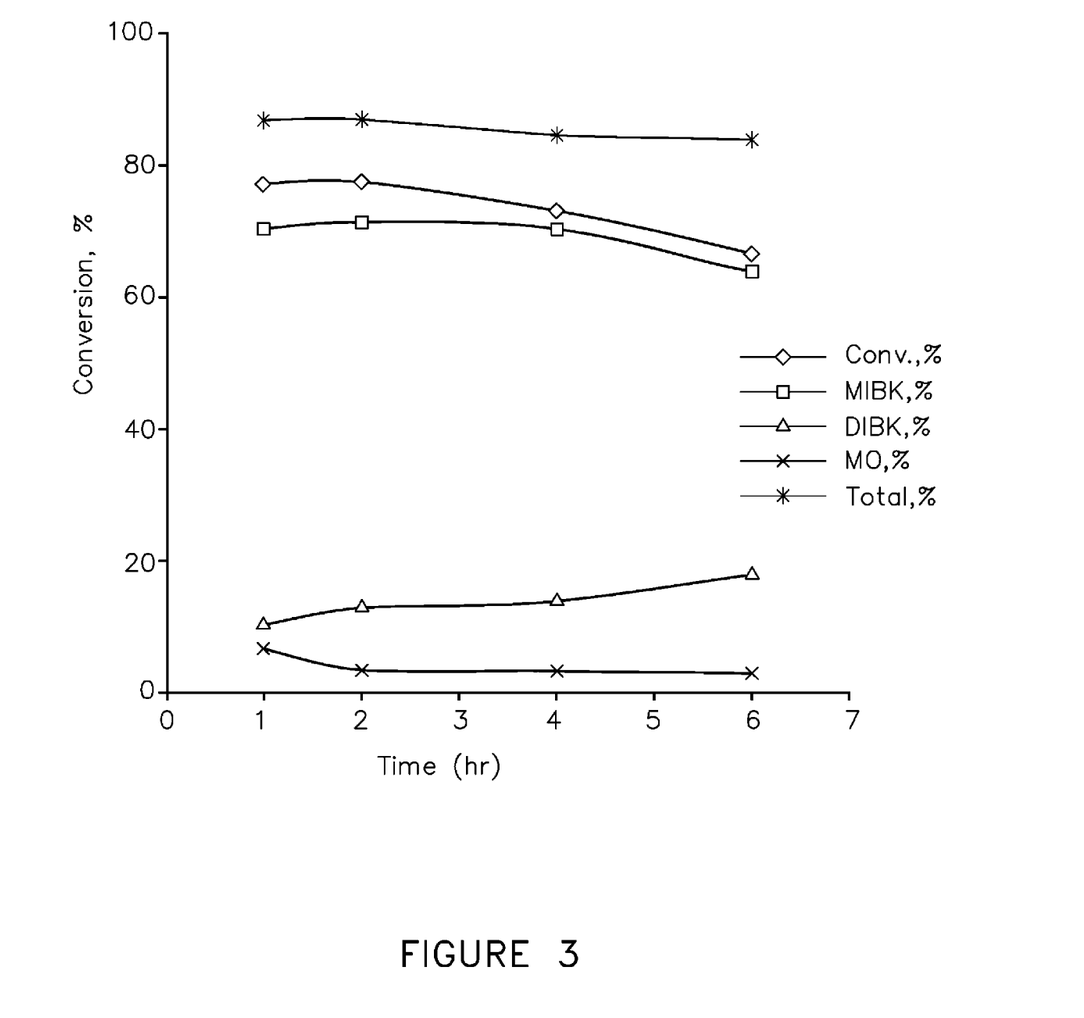
FIG. 3 shows Acetone conversion and product selectivity's vs. time on stream on 1% wt. n-Pd/n-ZnCr$_2$O$_4$ (0.25 g catalyst, 350° C., 15 ml/min H$_2$ flow, hydrogen/acetone=2/1 mol).
Figure 4:
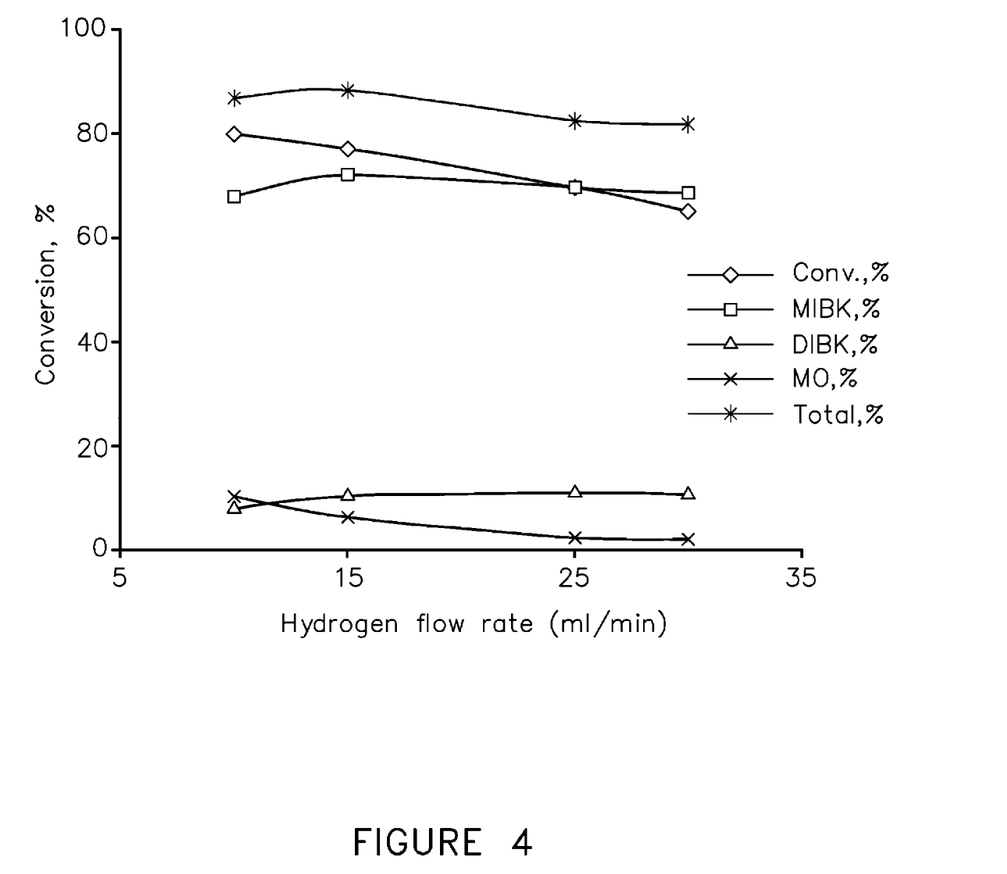
FIG. 4 shows results of Acetone conversion and product selectivity's vs. hydrogen flow rate on 1% wt. n-Pd/n-ZnCr$_2$O$_4$ (0.25 g catalyst, 350° C., time-1 hr).
Figure 5:
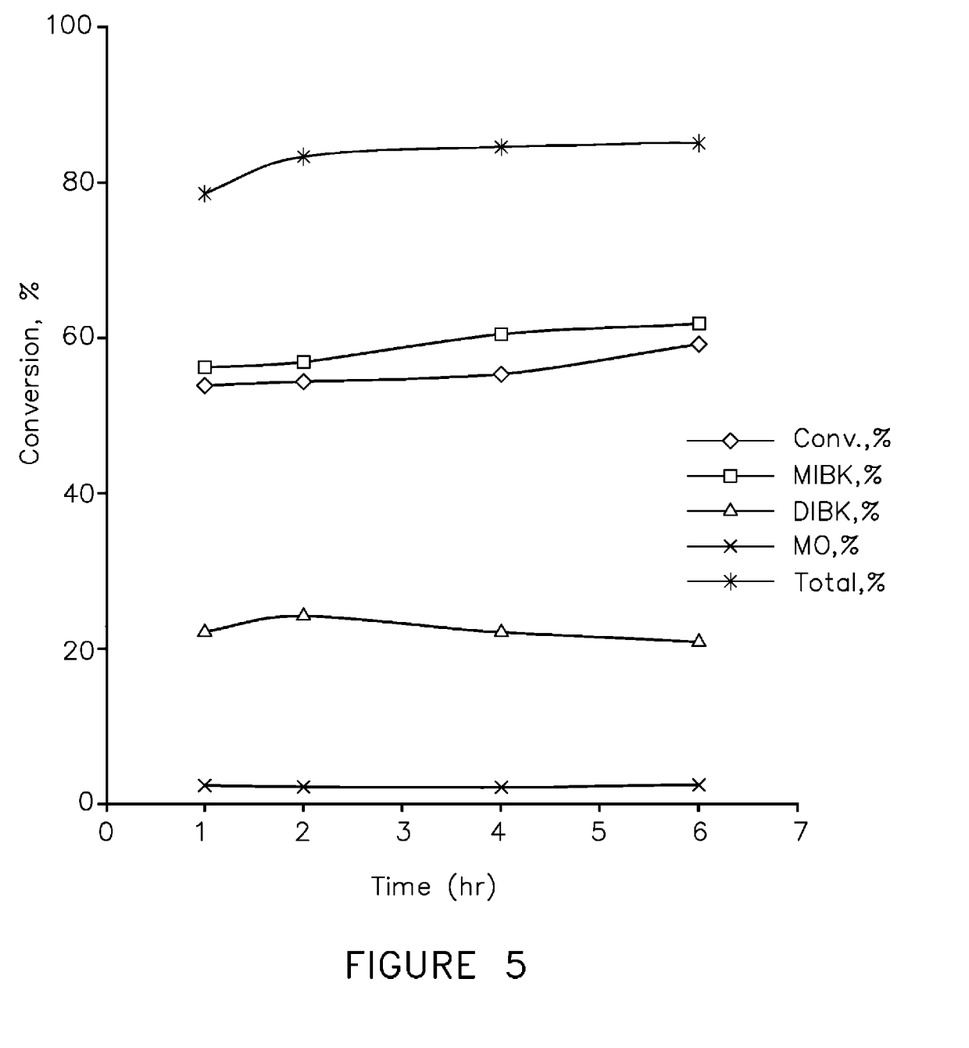
FIG. 5 shows the result of Acetone conversion and product selectivity's vs. time on stream on 1% wt. n-Pd/n-ZnO (0.25 g catalyst, 300° C., 15 ml/min H$_2$ flow, hydrogen/acetone=2/1 mol).

Pd was found to be the most effective among metals used for the hydrogenation function of catalysts. The 1% wt. n-Pd/n-ZnCr$_2$O$_4$ gave the most active and selective catalyst for direct synthesis of MIBK from acetone. The highest MIBK selectivity of 72.1% was obtained at 77.3 wt % acetone conversion at 350° C. The total MIBK and DIBK selectivity of 85.6% was obtained at these conditions (Table 5, FIG. 2).

n-Pd/n-ZnO without any other component was also selective catalyst for the synthesis of MIBK (selectivity 56.2%). When n-ZnCr$_2$O$_4$ was used in the N$_2$ atmosphere in the absence of hydrogen, MO was the major product. The same results were achieved when reaction was carried out on n-ZnCr$_2$O$_4$ under H$_2$ atmosphere in the absence of Pd. These results showed that the n-ZnCr$_2$O$_4$ itself acted mainly as an acidic-basic catalyst. The n-Pd/nano-ZnO and 1% wt. n-Pd/n-ZnCr$_2$O$_4$ catalysts exhibited very good stability (FIGS. 3-5). No catalyst deactivation was observed during 50 hours of continuous operation. With increasing reaction temperature, acetone conversion increased from 23.6% at 200° C. to 77.3% at 350° C. Under these conditions, MIBK selectivity also increased from 40.6.0% to 72.1%.

In addition, the specification and drawings are to be regarded in an illustrative rather than as in a restrictive sense.

What is claimed is:

1. A catalyst, comprising:
  a platinum group metal;
  a metal oxide; and
  a nano-zinc oxide.
2. The catalyst as in claim 1, wherein the platinum group of metal is at least one of ruthenium, rhodium, palladium, osmium, iridium, and platinum.
3. The catalyst as in claim 2, wherein the platinum group of metal is palladium acetate.
4. The catalyst as in claim 3, wherein palladium acetate is reduced to a nano-palladium.
5. The catalyst as in claim 1, wherein the metal oxide is a chromic oxide.
6. The catalyst as in claim 1, further comprising of a formula of n-Pd/n-ZnCr$_2$O$_4$.
7. A method of making a catalyst, comprising:
  reacting zinc sulfate heptahydrate, sodium pyruvate, sodium hydrogen carbonate and hydroxylamine hydrochloride to produce a nano-ZnO;
  calcinating the metal oxide under nitrogen flow to produce a metal oxide powder; and
  mixing the nano-ZnO and the metal oxide powder in a ratio to form a nano-ZnO-metal oxide mix.
8. The method of claim 7, further comprising:
  dissolving a platinum group metal salt in a thiophene-free benzene by mechanical stirring;
  mixing the nano-ZnO-metal oxide mix with the platinum group metal salt dissolved in thiophene-free benzene to form a pre-catalyst;
  evaporating the benzene under vacuum at ambient temperature using rotary evaporator to dry the pre-catalyst;
  reducing the dried pre-catalyst under a steady flow of hydrogen at 350° C. in a tubular muffle furnace;
  heating and cooling the pre-catalyst to obtain a catalyst by a reduction process; and
  storing the catalyst under at least one of nitrogen and argon in desiccators until further use.
9. The method of claim 7, wherein the metal oxide is a chromic oxide.
10. The method of claim 8, wherein the salt of platinum group of metal is at least one of ruthenium, rhodium, palladium, osmium, iridium, and platinum.
11. The method as in claim 9, wherein the salt of platinum group of metal is palladium acetate.
12. The method of claim 11, wherein palladium acetate is reduced to nano-palladium metal.
13. The method of claim 12, wherein the catalyst formed has a formula of 1% wt. n-Pd/n-ZnCr$_2$O$_4$.
14. A process, comprising;
  synthesizing a nano-ZnO;
  mixing a metal oxide to nano-ZnO;
  synthesizing a nano-palladium/nano-Zn-metal oxide catalyst; and
  producing at least one of a methyl isobutyl ketone, diisobutyl ketone, mesityl oxide, mesitylene and isopropyl alcohol using the nanopalladium/nano-Zn-metal oxide catalyst from acetone self-condensation.
15. The process of claim 14, wherein the metal oxide is chromic oxide (CrO$_3$).
16. The process of claim 14, further comprising:
  producing nano-ZnO by reacting zinc sulfate heptahydrate, sodium pyruvate, sodium hydrogen carbonate and hydroxylamine hydrochloride;

flowing steady stream of nitrogen over the metal oxide during the calcinations of metal oxide to produce a metal oxide powder; and synthesizing a nano-ZnO-metal-oxide mix by mixing a 1:1 mole ratio of the metal oxide powder and nano-ZnO.

17. The process of claim 14, further comprising:

mechanically stifling the platinum group of metal salt in thiophene-free benzene to make a metal-salt solution;

mixing the nano-ZnO-metal oxide mix with the platinum group metal salt dissolved in thiophene-free benzene to form a pre-catalyst;

performing rotary evaporation of the benzene under vacuum at ambient temperature to dry the pre-catalyst;

maintaining a steady flow of hydrogen in a known rate to reduce the pre-catalyst at 350° C.;

cooling and heating the pre-catalyst to obtain a catalyst by a reduction process; and storing the catalyst under at least one of nitrogen and argon in desiccators until further use.

18. The process of claim 17, further comprising:

placing a catalyst between two layers of pyrex glass wool and pieces of ceramic; and loading the catalyst into a reactor.

19. The process of claim 18, further comprising:

vaporizing acetone at a temperature between 65-70° C.;

mixing the vaporized acetone at least one of $H_2$ and $N_2$ gas as a mix;

pumping the mix in a continuous flow into the reactor under atmospheric pressure; and maintaining the temperature of the reactor between 250-350° C.

20. The process of claim 19, further comprising:

collecting a liquid product that was formed and analyzing the liquid product every hour using a gas chromatography equipment; and analyzing a gas product using a gas analyzer to identify and quantify the gas product.

* * * * *

UNITED STATES PATENT AND TRADEMARK OFFICE
CERTIFICATE OF CORRECTION

| | | |
|---|---|---|
| PATENT NO. | : 7,951,976 B1 | Page 1 of 1 |
| APPLICATION NO. | : 12/856653 | |
| DATED | : May 31, 2011 | |
| INVENTOR(S) | : Bagabas et al. | |

It is certified that error appears in the above-identified patent and that said Letters Patent is hereby corrected as shown below:

Title page, item [54] and Col. 1, lines 1-3

Title should read as follows:

SYNTHESIZING AND UTILIZING NOVEL NANO-CRYSTALLINE ZINC CHROMITE-SUPPORTED NANO-PALLADIUM CATALYST

Title page, item [75]

Inventor Name should read as follows:

Abdulrahman A. Al-Rabiah

Signed and Sealed this
Fifteenth Day of November, 2011

David J. Kappos
*Director of the United States Patent and Trademark Office*